United States Patent [19]
Honjo et al.

[11] Patent Number: 5,629,204
[45] Date of Patent: May 13, 1997

[54] PEPTIDE RELATED TO HUMAN PROGRAMMED CELL DEATH AND DNA ENCODING IT

[75] Inventors: Tasuku Honjo, Kyoto, Japan; Yasumasa Ishida, Newton, Mass.; Takashi Shinohara, Kyoto, Japan

[73] Assignees: Ono Pharmaceutical Co., Ltd., Osaka; Tasuku Honjo, Kyoto, both of Japan

[21] Appl. No.: 396,650

[22] Filed: Mar. 1, 1995

[30] Foreign Application Priority Data

Mar. 1, 1994 [JP] Japan .................................. 6-055224

[51] Int. Cl.$^6$ ............................ C12N 15/12; C12N 15/63
[52] U.S. Cl. ........................... 435/320.1; 935/9; 536/23.5
[58] Field of Search .................................. 536/23.5, 24.31, 536/24.33; 435/69.1, 320.1, 240.1, 252.33, 254.11

[56] References Cited

FOREIGN PATENT DOCUMENTS 5336973  12/1993  Japan .

OTHER PUBLICATIONS

EMBO Journal vol. 11 No. 11 pp. 3887–3895 (1992) Ishida et al.

*Primary Examiner*—Robert A. Wax
*Assistant Examiner*—G. E. Bugaisky
*Attorney, Agent, or Firm*—Sughrue, Mion, Zinn, Macpeak & Seas

[57] ABSTRACT

A membrane protein related to human programmed cell death (PD-1) and DNA encoding the said protein is provided. PD-1 protein may be useful for the treatment of various infections, immunological depression or acceleration, or tumors etc.

4 Claims, No Drawings

PEPTIDE RELATED TO HUMAN PROGRAMMED CELL DEATH AND DNA ENCODING IT

FIELD OF THE INVENTION

The present invention is directed to a novel peptide related to cell death and DNAs encoding the same.

BACKGROUND OF THE INVENTION

Developmentally and physiologically controlled cell death can be observed in almost all tissues of various species of animals. Such cell deaths are generally considered 'programmed' and are distinguishable from 'accidental' deaths that occur by pathological mechanisms. Most of the cells undergoing programmed death have been shown to require de novo synthesis of RNA and protein.

These facts suggest that at least a few genes, if not specified ones, must be expressed to cause programmed cell death.

The term "apoptosis", on the other hand, is used to describe the morphological characteristics of a class of cell death. In cells dying by apoptosis, chromatin condenses around the periphery of the nucleus, while mitochondria and other organelles are unaffected. A unique biochemical feature of apoptotic cells includes fragmentation of DNA into oligonucleosomal pieces. In mammals, apoptosis is often morphologically and biochemically associated with programmed cell death, but some of the cells undergoing programmed death apparently do not show the characteristic features of apoptosis. In addition, there are apoptotic cell deaths that can be induced in the absence of any protein synthesis.

Thus, it is important to note that apoptosis is not synonymous with programmed cell death.

It has recently become apparent that bcl-2, which is a oncogene, protects mortalized B cells from cell death, thus showing its importance to control cell death.

Certain peptides that are related to programmed cell death have been reported, such as the Fas antigen (Itoh et al, Cell, 66:233 (1991)).

Human Fas antigen is a polypeptide consisting of about 335 amino acids, having a signal peptide consisting of 16 hydrophobic amino acids N-terminal. Its mature protein is thought to have a structure divided into an extracellular domain (157 amino acids), a transmembrane region (17 amino acids) and a cytoplasmic domain (145 amino acids). It is thought to function as a receptor to a factor (ligand) inducing cell death.

SUMMARY OF THE INVENTION

An object of the present invention is to find novel polypeptides that are alternatives to polypeptides represented by the Fas antigen.

In this invention, a gene related to programmed cell death has been isolated, its nucleotide sequence determined and its amino acid sequence deduced. Thus, the present inventors have succeeded in isolating a novel polypeptide and the DNA encoding it.

To isolate a gene related to programmed cell death in humans, mouse PD-1, which was obtained from mouse T cell hybridoma 2B 4.11 (Japanese Patent Kokai 5-336973), was used as a probe.

There were no polypeptides having an amino acid sequence that is identical to or that has high homology to that of the polypeptide of the present invention, except for mouse PD-1, when amino acid sequences of the polypeptide identified in the present invention were searched by a computer program containing all known sequences in the data base of the National Biomedical Research Foundation. Needless to say, it was confirmed that the polypeptide of the present invention has no homology to the Fas antigen.

DETAILED DESCRIPTION OF THE INVENTION

The present invention is related to a polypeptide which is related to programmed cell death (abbreviated human PD-1 hereafter).

The present invention is directed to a polypeptide having the amino acid shown in SEQ ID NO:1, in substantially purified form, a homologue thereof or a fragment of the sequence or homologue of a fragment, and DNA encoding such a polypeptide. More particularly, the present invention is related to DNA having the nucleotide sequences shown in SEQ ID NOs:2 or 3, and DNA having a fragment which is able to selectively hybridize to the nucleotide sequences shown in SEQ ID NOs:2 or 3.

The present invention is related to:

(1) a polypeptide having an amino acid sequence shown in SEQ ID NO:1, (2) a DNA molecule encoding the polypeptide described above in (1), (3) a DNA molecule having a nucleotide sequence shown in SEQ ID NO:2, and (4) a DNA molecule having a nucleotide sequence shown in SEQ ID NO:3.

The polypeptide of SEQ ID NO:1 in substantially purified form will generally contain the polypeptide in a preparation in which more than 90%, e.g., 95%, 98% or 99% of the polypeptide in the preparation is that of SEQ ID NO:1.

A polypeptide homologue of SEQ ID NO:1 will be generally at least 70%, preferably at least 80 or 90%, and more preferably at least 95%, homologous to the polypeptide of SEQ ID NO:1 over a region of at least 20, preferably at least 30, for instance 40, 60 or 100, or more contiguous amino acids. Such polypeptide homologues will be referred to below as a polypeptide according to the invention.

Generally, fragments of SEQ ID NO:1 or its homologues will be at least 10, preferably at least 15, for example, 20, 25, 30, 40, 50 or 60 amino acids in length, and are also encompassed by the term "a polypeptide according to the invention" as used herein.

DNA capable of selectively hybridizing to the DNA of SEQ ID NOs:2 or 3 will be generally at least 70%, preferably at least 80 or 90%, and more preferably at least 95%, homologous to the DNA of SEQ ID NOs:2 or 3 over a region of at least 20, preferably at least 30, for instance 40, 60 or 100 or more contiguous nucleotides. Such DNA will be encompassed by the term "DNA according to the invention".

Fragments of the DNA of SEQ ID NOs:2 or 3 will be at least 15, preferably at least 20, for example, 25, 30 or 40 nucleotides in length, and are also encompassed by the term "DNA according to the invention" as used herein.

A further embodiment of the invention provides replication and expression vectors comprising DNA according to the invention. The vectors may be, for example, plasmid, virus or phage vectors provided with an origin of replication, optionally a promoter for the expression of the said DNA, and optionally a regulator of the promoter. The vector may contain one or more selectable marker genes, for example, an ampicillin resistance gene. The vector may be used in vitro, for example, for the production of RNA corresponding to the DNA, or used to transfect or transform a host cell.

A further embodiment of the invention provides host cells transformed or transfected with the vectors for the replication and expression of DNA according to the invention, including DNA SEQ ID NOs:2 or 3 or the open reading frame thereof. The cells chosen are to be compatible with the vector and may, for example, be bacterial, yeast, insect or mammalian.

A further embodiment of the invention provides a method of producing a polypeptide, which comprises culturing host cells of the present invention under conditions effective to express a polypeptide according to the invention. Preferably, in addition, such a method is carried out under conditions in which the polypeptide of the invention is expressed and then produced from the host cells.

DNA according to the invention may also be inserted into the vectors described above, in an antisense orientation in order to provide for the production of antisense RNA. Antisense RNA may also be produced by synthetic means. Such antisense RNA may be used in a method for controlling the level of a polypeptide of the invention in a cell.

The invention also provides monoclonal or polyclonal antibodies to a polypeptide according to the invention. The invention further provides a process for the production of monoclonal or polyclonal antibodies to the polypeptides of the invention. Monoclonal antibodies may be prepared by conventional hybridoma technology using a polypeptide of the invention or a fragment thereof, as an immunogen. Polyclonal antibodies may also be prepared by conventional means which comprise inoculating a host animal, for example, a rat or a rabbit, with a polypeptide of the invention and recovering immune serum.

The present invention also provides pharmaceutical compositions containing a polypeptide of the invention, or an antibody thereof, in association with a pharmaceutically acceptable diluent and/or carrier.

A polypeptide of the present invention includes one in which a part of its amino acid sequence is missing (e.g., a polypeptide containing only the sequence essential for biological activity from the amino acid sequence shown in SEQ ID NO:1), one in which a part of its amino acid sequence is replaced by other amino acids (e.g., those replaced by an amino acid having a similar property), and one in which other amino acids are added or inserted into a part of its amino acid sequence, as well as those having the amino acid sequence shown in SEQ ID NO:1.

As is well-known, there are one to six codons that may encode an amino acid (for example, one codon for Methioine (Met), and six codons for leucine (Leu) are known). Accordingly, the DNA sequence can be changed, yet still encode the polypeptide having the same amino acid sequence.

The DNA of the present invention, specified in (2) above includes the group of every nucleotide sequence encoding polypeptide (1) shown in SEQ ID NO:1. There is a probability that the production yield of a polypeptide can be improved by changing the nucleotide sequence.

The DNA specified in (3) above, is an embodiment of the DNA shown in (2), and is the natural form of the sequence.

The DNA shown in (4) above, indicates the sequence of the DNA specified in (3) having a non-translational region.

The DNA of the present invention may be obtained by gene recombination, chemical synthesis or known methods by those skilled in the art.

Human PD-1 includes a series of polypeptides that are different from the Fas antigen in structural features and occur commonly in mammals. That is, PD-1 of the present invention includes human PD-1 recited in the present invention and PD-1 of other mammals that have high homology (meaning an immunological equivalent that can be cross-reacted to human PD-1 antigen).

The structural features of human PD-1 are as follows:

Human PD-1 is predicted to be a membrane binding type protein consisting of 288 amino acids. It contains two hydrophobic regions, one at the N-terminus and the other in the middle, which are likely to serve as a signal peptide and a transmembrane segment, respectively.

Comparison of the N-terminal sequence of the PD-1 protein with typical signal peptide cleavage sites suggests that the signal peptide would be located from $Met_1$ to $Arg_{20}$. Thus, the predicted mature form of the PD-1 protein would contain 268 amino acids and consist of an extracellular domain (147 amino acids), a transmembrane region (27 amino acids) and a cytoplasmic domain (94 amino acids). Four potential N-glycosylation sites are found in the putative extracellular domain.

Comparison of the amino acid sequence of the PD-1 protein with all sequences registered in the National Biomedical Research Foundation data base revealed that the extracellular domain of the PD-1 protein is homologous to some members of the immunoglobulin superfamily. Immunoglobulin domains have been classified into V, C1 and C2 sets based on conserved amino acid patterns and the number of antiparallel beta-strands. The 68 amino acid residues between two cysteine residues ($Cys_{54}$ and $Cys_{123}$) in PD-1 bear resemblance to a disulfide-linked immunoglobulin domain of the V-set sequences. In addition, all of the four amino acid residues characteristic of many V-set sequences are also conserved in PD-1 ($Arg_{94}$, $Phe_{95}$, $Asp_{117}$ and $Gly_{119}$).

The cytoplasmic domain of the predicted PD-1 protein contains a variant form of the consensus sequence (Asp/Glu-X8-Asp/Glu-X2-Tyr-X2-Leu/Ile-X7-Tyr-X2-Leu/Ile) found in the cytoplasmic tails of most of the polypeptides associated with antigen receptors and Fc receptors. It was recently shown that one signal unit of this consensus sequence is sufficient to transduce signals.

It is thought that PD-1 of other mammals would be similar to human PD-1 in structural feature, whether or not the number or types of its amino acids would be different.

DNA encoding human PD-1 of the present invention may be prepared by the following method.

Once the nucleotide sequences shown in SEQ ID NOs:2 and 3 are determined, DNA of the present invention may be obtained by chemical synthesis, by the PCR method or by hybridization making use of a fragment of DNA of the present invention, as a probe. Furthermore, DNA of the present invention may be obtained in a desired amount by transforming a proper host with a DNA vector which has inserted therein a DNA of the present invention, followed by culturing the transformant.

PD-1 polypeptides of the present invention (shown in SEQ ID NO:1) may be prepared by:

(1) isolating and purifying from an organism or a cultured cell, (2) chemically synthesizing, or (3) using a biotechnological procedure, preferably, by the method described in (3).

Examples of the expression systems that may be used when preparing a polypeptide by using a biotechnological procedure are, for example, the expression systems of bacteria, yeast, insects and mammalian cells.

For example, expression in *E. coli* may be carried out by adding the initiation codon (ATG) to the 5' end of a DNA encoding a mature peptide, connecting the DNA thus obtained to the downstream end of a proper promoter (e.g., trp promoter, lac promoter, λ PL promoter, T7 promoter), and then inserting it into a vector (e.g., pBR322, pUC18, pUC19) that functions in an *E. coli* strain, to prepare an expression vector.

Then, an *E. coli* strain (e.g., *E. coli* strain DH1, *E. coli* strain JM109, *E. coli* strain HB101) that is transformed with the expression vector thus obtained may be cultured in a proper medium to obtain the desired polypeptide. When a signal peptide of bacteria (e.g., signal peptide of pel B) is used, the desired polypeptide may be also be released in the periplasm. Furthermore, a fusion protein with another polypeptide may also be easily produced.

Furthermore, expression in a mammalian cell may be carried out, for example, by inserting the total DNA encoding PD-1 downstream of a proper promoter (e.g., SV40 promoter, LTR promoter, metallothionein promoter) in a proper vector (e.g., retrovirus vector, papilloma virus vector, vaccinia virus vector, SV40 vector, etc.) to obtain an expression vector, and transforming a proper mammalian cell (e.g., monkey COS-7 cell, Chinese hamster CHO cell, mouse L cell) with the expression vector thus obtained, and then culturing the transformant in a proper medium to obtain a desired polypeptide in the culture medium. The polypeptide thus obtained may be isolated and purified by conventional biochemical methods.

DNA encoding the PD-1 gene obtained by the present invention may be used as a probe for the isolation of PD-1 genes of other animals.

cDNA having a nucleotide sequence shown in SEQ ID NO:3 may be prepared according to the following methods, that is:

(i) isolating mRNA from a cell line which produces the polypeptide of the present invention (e.g., human esophageal cancer cell line), (ii) preparing first strand (single stranded DNA) from the mRNA thus obtained, followed by preparing a second strand (double stranded DNA) (synthesis of cDNA), (iii) inserting the cDNA thus obtained into a proper phage vector, (iv) transforming host cells with the recombinant DNA thus obtained (preparation of cDNA library), (v) screening the cDNA library thus obtained with cDNA of mouse PD-1 as a probe using plaque hybridization, (vi) preparing phage DNA from the positive clone obtained, subcloning the cDNA released into a plasmid vector, preparing a restriction enzyme map, and (vii) determining the sequence of each restriction enzyme fragment, and obtaining the full sequence of the complete length by combining them.

Step (i) may be carried out in accordance with the method of Okayama et al (*Methods in Enzymology*, 154:3 (1987)) from a human cell line after stimulation by a proper stimulant (e.g., IL-1) or without stimulation. A cell which produces the polypeptide of the present invention is preferably the human cell line YTC3.

Steps (ii), (iii) and (iv) are a series of steps for preparing a cDNA library, and may be carried out in accordance with the method of Gubler & Hoffman, (Gene, 25:263 (1983)) with a slight modification. As examples of the plasmid vector used in the step (iii), many plasmid vectors (e.g., pBR322, pBluescript II) and phage vectors (e.g., λ gt10, λ DASH II) are known, and phage vector λ gt10 (43.3 kbp; Stratagene) may be preferably used.

As the host cell used in step (iv), *E. coli* NM514 (Stratagene) may be preferably used.

Steps (v) and (vi) may be carried out in accordance with the method described in Molecular Cloning (Sambrook et al, Cold Spring Harbor Laboratory Press (1989)).

Step (vii) may be carried out in accordance with the method described in Molecular Cloning (Sambrook et al, supra).

The sequencing in step (vii) may be carried out in accordance with the method of Maxam-Gilbert or the dideoxy termination method.

It is necessary to determine whether or not the cDNA thus obtained codes for a complete or almost complete length. The confirmation may be carried out by a Northern analysis using said cDNA as a probe (see Molecular Cloning, supra). It is thought that a cDNA is almost full-length, if the length of the cDNA is almost the same as the length of the mRNA obtained in the hybridizing band.

DNA or DNA fragments encoding the PD-1 gene may be used as a probe or primer for detection of a PD-1 gene and thereby, and may be utilized to investigate the relationship between said polypeptide and a protection mechanism in the living organism, an immunological function or a disease, like a tumor, or for the purpose of diagnosing diseases.

The DNA of the present invention may be used as an important and essential template in preparing, by conventional gene recombination, the PD-1 polypeptide, polypeptide fragment thereof or derivatives thereof that are expected to possess various uses.

It is expected that the polypeptide, polypeptide fragments thereof or derived polypeptides thereof may be used for the treatment of infections, depression or acceleration of immunological functions or tumors.

Further, polyclonal and monoclonal antibodies against the polypeptide or polypeptide fragments of the present invention can be prepared by conventional methods, and they can be used to quantitate said polypeptide in an organism, and thereby, may be used to investigate the relationship between said polypeptide and diseases, or for the purpose of diagnosing diseases. Said monoclonal antibody per se, a chimeric antibody against the human antibody, may be used as a treating agent. A polyclonal and monoclonal antibody thereof may be prepared by conventional methods by using the polypeptide or a fragment thereof as an antigen.

The polypeptide of the present invention may be administered systemically or partially, usually by oral or parenteral administration, preferably orally, intravenously or intraventricularly.

The dosage to be administered will vary depending upon age, body weight, symptoms, the desired therapeutic effect, the route of administration, and the duration of the treatment. In the human adult, the dosage per person per dose is generally between 100 μg and 100 mg, by oral administration, up to several times per day, and between 10 μg and 100 mg, by parenteral administration up to several times per day.

As mentioned above, the dose to be used depends upon various conditions. Therefore, there are cases in which dosages lower than or greater than the ranges specified above may be used.

Administration of compounds of the present invention, may be as solid compositions, liquid compositions or other compositions for oral administration, or as injections, liniments or suppositories for parenteral administration.

Solid compositions for oral administration include compressed tablets, pills, capsules, dispersible powders and granules. Capsules include soft capsules and hard capsules.

In such compositions, one or more of the active compound(s) is or are admixed with at least one inert diluent (such as, lactose, mannitol, glucose, hydroxypropyl cellulose, microcrystalline cellulose, starch, polyvinylpyrrolidone, and magnesium metasilicate aluminate). The compositions may also comprise, as is normal practice, additional substances other than inert diluents, e.g., lubricating agents (such as, magnesium stearate), disintegrating agents (such as, cellulose calcium glycolate), stabilizing agents (such as, human serum albumin and lactose), and agents to assist dissolving (such as, arginine and asparaginic acid).

The tablets or pills may, if desired, be coated with a film of gastric or enteric material (such as sugar, gelatin, hydroxypropyl cellulose or hydroxypropylmethyl cellulose phthalate), or be coated with more than two films. And further, coating may include containment within capsules of absorbable materials, such as gelatin.

Liquid compositions for oral administration include pharmaceutically-acceptable emulsions, solutions, syrups and elixirs. In such compositions, one or more of the active compound(s) is or are contained in inert diluent(s) commonly used in the art (e.g., purified water, ethanol). Besides inert diluents, such compositions may also comprise adjuvants (such as, wetting agents and suspending agents), sweetening agents, flavoring agents, perfuming agents, and preserving agents.

Other compositions for oral administration include spray compositions which may be prepared by known methods and which comprise one or more of the active compound(s). Spray compositions may comprise additional substances other than inert diluents, e.g., stabilizing agents (sodium sulfite), isotonic buffer (sodium chloride, sodium citrate and citric acid). For preparation of such spray compositions, for example, the method described in U.S. Pat. No. 2,868,691 or 3,095,355 (herein incorporated by reference in their entireties) may be used.

Injections for parenteral administration include sterile aqueous or non-aqueous solutions, suspensions and emulsions. In such compositions, one or more active compound (s) is or are admixed with at least one inert aqueous diluent(s) (distilled water for injection, physiological salt solution) or inert non-aqueous diluents(s)(propylene glycol, polyethylene glycol, olive oil, ethanol, POLYSOLBATE 80™).

Injections may comprise additional agents other than inert diluents: e.g., preserving agents, wetting agents, emulsifying agents, dispersing agents, stabilizing agents (such as, human serum albumin and lactose), and assisting agents, such as agents to assist dissolving (arginine and asparaginic acid).

They may be sterilized, for example, by filtration through a bacteria-retaining filter, by incorporation of sterilizing agents in the compositions or by irradiation. They may also be manufactured in the form of sterile solid compositions, for example, by freeze-drying, that can be dissolved in sterile water or some other sterile diluent for injection immediately before use.

Other compositions for parenteral administration include liquids for external use, and endermic liniments (ointment), suppositories for rectal administration and pessaries which comprise one or more of the active compound(s) and may be prepared by known methods.

The following examples are provided for illustrative purposes only, and are in no way intended to limit the scope of the present invention.

EXAMPLE 1

Cell Culture

Human cell lines (CESS, HPB-ALL, Jarkat, TC3, CCRF-CEM, JM and MOLT-4F) were cultured in RPMI 1640 (Gibco) supplemented with 10% heat-inactivated fetal calf serum, 2.0 mM glutamine, 50 µM 2-mercaptoethanol, 100 U/ml penicillin and 100 µg/ml streptomycin.

EXAMPLE 2

Northern Blot Analysis

Total RNA was prepared from the indicated cell lines by extraction according to the guanidium isothiocyanate method (see Molecular Cloning, supra), and poly (A)+RNA was isolated from total RNA by oligotex-dT$^{30}$ (Daiichi Chemical Co.). 3 µg of poly (A)+ RNA was separated on a 1.2% formaldehyde-agarose gel, and transferred to a nylon membrane (Biodyne A, Japan Genetic). The filter was baked at 80° C. for 2 hrs. Random priming was carried using to the EcoRI fragment (1 kb) containing the coding region of mouse PD-1, as a probe labeled with $^{32}$P. The specific activity of this probe was about $9\times10^8$ d.p.m./µg. Hybridization was carried out in 10×Denhardt's, 1.0M NaCl, 50 mM Tris (pH 7.5), 10 mM EDTA, 1.0% SDS and 1.0 mg/ml sonicated salmon sperm DNA at 65° C. for 15 hrs. The filter was washed in 1×SSC, 0.1% SDS at 65° C. for 10 min. A hybridization signal (2.3 kb) was observed from the lymphocyte cell line YTC3 by autoradiography.

EXAMPLE 3

Construction of cDNA Library and Cloning of Human PD-1 cDNA

The cDNA library was constructed with 5 µg of poly (A)+RNA extracted from YTC3 cell lines by using Time Saver cDNA Synthesis Kit (Pharmacia). Synthesis of the first strand of cDNA was carried out with oligo dT primer. Double stranded cDNA, which was ligated to an EcoRI-NotI adapter, was cloned into λ gt 10 vector, and packaged into phage (Gigapack II Gold, Stratagene). Phage was plated on a lawn of *E. coli* NM514. Phage DNA was transfected to duplicated library filters from each plate. The filters were baked at 80° C. for 2 hrs and hybridized at 60° C. for 15 hrs. The mouse PD-1 coding region (1 kb) excised with EcoRI from Bluescript SK plasmid vector (Stratagene) was used as a probe. The filter was washed with 1×SSC and 0.1% SDS at 60° C. for 10 mins. 51-Positive signals were observed from $1.2\times10^6$ phages by autoradiography. These clones were purified. Further analysis was carried out, about 23 clones were picked, the longest cDNA insert observed was 2.1 kb. This result coincided with the results of the Southern blot analysis.

EXAMPLE 4

Sequencing of DNA

The cDNA inserts isolated from the human cDNA library were subcloned into Bluescript SK plasmid vectors (Stratagene), and sequenced by the dideoxynucleotide chain termination method (Sanger et al (1977)) using a modified T7 DNA polymerase (United States Biochemical) and

[α-³²P]dCTP (3000 Ci/mmol, Amersham). The specific primer of Bluescript plasmid was used as a sequencing primer. Nucleotide sequencing was carried out by fully sequencing for both strands of the cDNA and the nucleotide sequence shown in SEQ ID NO:2 was obtained. The deduced peptide sequence (shown in SEQ ID NO:1) was determined from the nucleotide sequence. The total number of deduced amino acids is 288, which is the same as that of mouse PD-1. Homology between the two was found to be about 60%.

EXAMPLE 5

Southern Blotting

Genomic DNA was isolated from different kinds of animal cells by a conventional method (see Molecular Cloning, supra). DNAs were digested with EcoRI, BamHI or HindIII according to the manufacturer's-recommendation, and isolated by electrophoresis (100 V, 0.8% agarose gel, TEA buffer). DNA fragments were washed with 0.25 N HCl for 10 min., denatured with 0.2 N NaOH/0.6M NaCl for 30 min., neutralized with 0.6M NaCl/0.2 M Tris (pH 7.5) for 1 hr., and transferred to nylon membranes (Bidyne A), which is standard Southern blot procedure. The filter were baked for 2 hrs.

Random priming was carried with the EcoRI-StuI fragment (900 bp) containing the coding region of human PD-1, using $^{32}$P. The specific activity of this probe was about 9×10⁸ d.p.m./μg. Hybridization was carried out in 10×Denhardt's, 1.0M NaCl, 50 mM Tris (pH 7.5), 10 mM EDTA, 1.0% SDS and 1.0 mg/ml sonicated salmon sperm DNA at 65° C. for 10 min. The filter was washed in 1×SSC, 0.1% SDS at 65° C. for 10 min. Only one band was detected by autoradiography, when the clone was cut with any enzyme. Thus, it was found that the human PD-1 gene exists as a single copy.

Southern hybridization was carried out with genomic DNA of different kinds of animals under the same conditions (hybridization and washing) described in Example 2, using the EcoRI fragment (1 kb) containing the coding region of mouse PD-1 as a probe. Hybridization signals were detected only from genomic DNA of mouse and human, and were not detected from genomic DNA of Drosophila, Xenopus and rabbit.

EXAMPLE 6

Isolation of Genomic Clone of Human PD-1

A genomic DNA library from an esophageal cancer cell line was constructed in the λ DASH II vector via Sau3AI partial digestion and ligation into the BamHI site (obtained from Dr. Nishiyama, 1st Dept. of Pathology, School of Medicine, Kyoto University). The human PD-1 gene was isolated from this library by hybridization with the human PD-1, total cDNA was excised by EcoRI digestion from a Bluescript SK vector. The probe was labeled with $^{32}$P by random priming. Two positive clones was isolated and purified from 1×10⁶ phage plaques, digested by several restriction enzymes, and analyzed by Southern hybridization using the same probe. From CISS (chromosomal in situ suppression), it was found that the human PD-1 gene mapped on 2q37.3.

---

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 288 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Met Gln Ile Pro Gln Ala Pro Trp Pro Val Val Trp Ala Val Leu Gln
 1               5                  10                  15

Leu Gly Trp Arg Pro Gly Trp Phe Leu Asp Ser Pro Asp Arg Pro Trp
             20                  25                  30

Asn Pro Pro Thr Phe Ser Pro Ala Leu Leu Val Val Thr Glu Gly Asp
         35                  40                  45

Asn Ala Thr Phe Thr Cys Ser Phe Ser Asn Thr Ser Glu Ser Phe Val
     50                  55                  60

Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
```

|     |     |     |     |     | 85  |     |     |     |     | 90  |     |     |     |     | 95  |     |     |
| --- | --- | --- | --- | --- | --- | --- | --- | --- | --- | --- | --- | --- | --- | --- | --- | --- | --- |
| Val | Thr | Gln | Leu 100 | Pro | Asn | Gly | Arg 105 | Asp | Phe | His | Met | Ser | Val 110 | Val | Arg |
| Ala | Arg | Arg 115 | Asn | Asp | Ser | Gly | Thr 120 | Tyr | Leu | Cys | Gly | Ala 125 | Ile | Ser | Leu |
| Ala | Pro 130 | Lys | Ala | Gln | Ile | Lys 135 | Glu | Ser | Leu | Arg | Ala 140 | Glu | Leu | Arg | Val |
| Thr 145 | Glu | Arg | Arg | Ala | Glu 150 | Val | Pro | Thr | Ala | His 155 | Pro | Ser | Pro | Ser | Pro 160 |
| Arg | Ser | Ala | Gly | Gln 165 | Phe | Gln | Thr | Leu | Val 170 | Gly | Val | Val | Gly 175 | Gly |
| Leu | Leu | Gly | Ser 180 | Leu | Val | Leu | Leu | Val 185 | Trp | Val | Leu | Ala | Val 190 | Ile | Cys |
| Ser | Arg | Ala 195 | Ala | Arg | Gly | Thr | Ile 200 | Gly | Ala | Arg | Arg | Thr 205 | Gly | Gln | Pro |
| Leu | Lys 210 | Glu | Asp | Pro | Ser | Ala 215 | Val | Pro | Val | Phe | Ser 220 | Val | Asp | Tyr | Gly |
| Glu 225 | Leu | Asp | Phe | Gln | Trp 230 | Arg | Glu | Lys | Thr | Pro 235 | Glu | Pro | Pro | Val | Pro 240 |
| Cys | Val | Pro | Glu | Gln 245 | Thr | Glu | Tyr | Ala | Thr 250 | Ile | Val | Phe | Pro | Ser 255 | Gly |
| Met | Gly | Thr | Ser 260 | Ser | Pro | Ala | Arg | Arg 265 | Gly | Ser | Ala | Asp | Gly 270 | Pro | Arg |
| Ser | Ala | Gln 275 | Pro | Leu | Arg | Pro | Glu 280 | Asp | Gly | His | Cys | Ser 285 | Trp | Pro | Leu |

( 2 ) INFORMATION FOR SEQ ID NO:2:

( i ) SEQUENCE CHARACTERISTICS:
        ( A ) LENGTH: 864 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

| | | | | | |
|---|---|---|---|---|---|
| ATGCAGATCC | CACAGGCGCC | CTGGCCAGTC | GTCTGGGCGG | TGCTACAACT | GGGCTGGCGG | 60 |
| CCAGGATGGT | TCTTAGACTC | CCCAGACAGG | CCCTGGAACC | CCCCCACCTT | CTCCCCAGCC | 120 |
| CTGCTCGTGG | TGACCGAAGG | GGACAACGCC | ACCTTCACCT | GCAGCTTCTC | CAACACATCG | 180 |
| GAGAGCTTCG | TGCTAAACTG | GTACCGCATG | AGCCCCAGCA | ACCAGACGGA | CAAGCTGGCC | 240 |
| GCCTTCCCCG | AGGACCGCAG | CCAGCCCGGC | CAGGACTGCC | GCTTCCGTGT | CACACAACTG | 300 |
| CCCAACGGGC | GTGACTTCCA | CATGAGCGTG | GTCAGGGCCC | GGCGCAATGA | CAGCGGCACC | 360 |
| TACCTCTGTG | GGGCCATCTC | CCTGGCCCCC | AAGGCGCAGA | TCAAAGAGAG | CCTGCGGGCA | 420 |
| GAGCTCAGGG | TGACAGAGAG | AAGGGCAGAA | GTGCCCACAG | CCCACCCCAG | CCCCTCACCC | 480 |
| AGGTCAGCCG | GCCAGTTCCA | AACCCTGGTG | GTTGGTGTCG | TGGGCGGCCT | GCTGGGCAGC | 540 |
| CTGGTGCTGC | TAGTCTGGGT | CCTGGCCGTC | ATCTGCTCCC | GGGCCGCACG | AGGGACAATA | 600 |
| GGAGCCAGGC | GCACCGGCCA | GCCCCTGAAG | GAGGACCCCT | CAGCCGTGCC | TGTGTTCTCT | 660 |
| GTGGACTATG | GGGAGCTGGA | TTTCCAGTGG | CGAGAGAAGA | CCCCGGAGCC | CCCCGTGCCC | 720 |
| TGTGTCCCTG | AGCAGACGGA | GTATGCCACC | ATTGTCTTTC | CTAGCGGAAT | GGGCACCTCA | 780 |
| TCCCCCGCCC | GCAGGGGCTC | AGCTGACGGC | CCTCGGAGTG | CCCAGCCACT | GAGGCCTGAG | 840 |
| GATGGACACT | GCTCTTGGCC | CCTC | | | | 864 |

( 2 ) INFORMATION FOR SEQ ID NO:3:

( i ) SEQUENCE CHARACTERISTICS:
        ( A ) LENGTH: 921 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

| | | | | | | |
|---|---|---|---|---|---|---|
| CACTCTGGTG | GGGCTGCTCC | AGGCATGCAG | ATCCCACAGG | CGCCCTGGCC | AGTCGTCTGG | 60 |
| GCGGTGCTAC | AACTGGGCTG | GCGGCCAGGA | TGGTTCTTAG | ACTCCCAGA | CAGGCCCTGG | 120 |
| AACCCCCCA | CCTTCTCCCC | AGCCCTGCTC | GTGGTGACCG | AAGGGACAA | CGCCACCTTC | 180 |
| ACCTGCAGCT | TCTCCAACAC | ATCGGAGAGC | TTCGTGCTAA | ACTGGTACCG | CATGAGCCCC | 240 |
| AGCAACCAGA | CGGACAAGCT | GGCCGCCTTC | CCCGAGGACC | GCAGCCAGCC | CGGCCAGGAC | 300 |
| TGCCGCTTCC | GTGTCACACA | ACTGCCCAAC | GGGCGTGACT | TCCACATGAG | CGTGGTCAGG | 360 |
| GCCCGGCGCA | ATGACAGCGG | CACCTACCTC | TGTGGGGCCA | TCTCCCTGGC | CCCCAAGGCG | 420 |
| CAGATCAAAG | AGAGCCTGCG | GGCAGAGCTC | AGGGTGACAG | AGAAGGGC | AGAAGTGCCC | 480 |
| ACAGCCCACC | CCAGCCCCTC | ACCCAGGTCA | GCCGGCCAGT | TCCAAACCCT | GGTGGTTGGT | 540 |
| GTCGTGGGCG | GCCTGCTGGG | CAGCCTGGTG | CTGCTAGTCT | GGGTCCTGGC | CGTCATCTGC | 600 |
| TCCCGGGCCG | CACGAGGGAC | AATAGGAGCC | AGGCGCACCG | GCCAGCCCCT | GAAGGAGGAC | 660 |
| CCCTCAGCCG | TGCCTGTGTT | CTCTGTGGAC | TATGGGGAGC | TGGATTTCCA | GTGGCGAGAG | 720 |
| AAGACCCCGG | AGCCCCCCGT | GCCCTGTGTC | CCTGAGCAGA | CGGAGTATGC | CACCATTGTC | 780 |
| TTTCCTAGCG | GAATGGGCAC | CTCATCCCCC | GCCCGCAGGG | CTCAGCTGA | CGGCCCTCGG | 840 |
| AGTGCCCAGC | CACTGAGGCC | TGAGGATGGA | CACTGCTCTT | GGCCCTCTG | ACCGGCTTCC | 900 |
| TTGGCCACCA | GTGTTCTGCA | G | | | | 921 |

( 2 ) INFORMATION FOR SEQ ID NO:4:

( i ) SEQUENCE CHARACTERISTICS:
        ( A ) LENGTH: 921 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens
        ( H ) CELL LINE: YTC3

( i x ) FEATURE:
        ( A ) NAME/KEY: CDS
        ( B ) LOCATION: 25..888
        ( C ) IDENTIFICATION METHOD: by similarity to some other pattern ( i x ) FEATURE:
        ( A ) NAME/KEY: sig_peptide
        ( B ) LOCATION: 25..84
        ( C ) IDENTIFICATION METHOD: by similarity with known sequence
            or to an established consensus ( i x ) FEATURE:
        ( A ) NAME/KEY: mat_peptide
        ( B ) LOCATION: 85..888
        ( C ) IDENTIFICATION METHOD: by similarity with known sequence
            or to an established consensus ( x i ) SEQUENCE DESCRIPTION: SEQ ID NO:4:

| | | |
|---|---|---|
| CACTCTGGTG GGGCTGCTCC AGGC ATG CAG ATC CCA CAG GCG CCC TGG CCA<br>Met Gln Ile Pro Gln Ala Pro Trp Pro<br>-20 -15 | | 51 |
| GTC GTC TGG GCG GTG CTA CAA CTG GGC TGG CGG CCA GGA TGG TTC TTA<br>Val Val Trp Ala Val Leu Gln Leu Gly Trp Arg Pro Gly Trp Phe Leu<br>-10 -5 1 5 | | 99 |
| GAC TCC CCA GAC AGG CCC TGG AAC CCC CCC ACC TTC TCC CCA GCC CTG<br>Asp Ser Pro Asp Arg Pro Trp Asn Pro Pro Thr Phe Ser Pro Ala Leu<br>10 15 20 | | 147 |
| CTC GTG GTG ACC GAA GGG GAC AAC GCC ACC TTC ACC TGC AGC TTC TCC<br>Leu Val Val Thr Glu Gly Asp Asn Ala Thr Phe Thr Cys Ser Phe Ser<br>25 30 35 | | 195 |
| AAC ACA TCG GAG AGC TTC GTG CTA AAC TGG TAC CGC ATG AGC CCC AGC<br>Asn Thr Ser Glu Ser Phe Val Leu Asn Trp Tyr Arg Met Ser Pro Ser<br>40 45 50 | | 243 |
| AAC CAG ACG GAC AAG CTG GCC GCC TTC CCC GAG GAC CGC AGC CAG CCC<br>Asn Gln Thr Asp Lys Leu Ala Ala Phe Pro Glu Asp Arg Ser Gln Pro<br>55 60 65 | | 291 |
| GGC CAG GAC TGC CGC TTC CGT GTC ACA CAA CTG CCC AAC GGG CGT GAC<br>Gly Gln Asp Cys Arg Phe Arg Val Thr Gln Leu Pro Asn Gly Arg Asp<br>70 75 80 85 | | 339 |
| TTC CAC ATG AGC GTG GTC AGG GCC CGG CGC AAT GAC AGC GGC ACC TAC<br>Phe His Met Ser Val Val Arg Ala Arg Arg Asn Asp Ser Gly Thr Tyr<br>90 95 100 | | 387 |
| CTC TGT GGG GCC ATC TCC CTG GCC CCC AAG GCG CAG ATC AAA GAG AGC<br>Leu Cys Gly Ala Ile Ser Leu Ala Pro Lys Ala Gln Ile Lys Glu Ser<br>105 110 115 | | 435 |
| CTG CGG GCA GAG CTC AGG GTG ACA GAG AGA AGG GCA GAA GTG CCC ACA<br>Leu Arg Ala Glu Leu Arg Val Thr Glu Arg Arg Ala Glu Val Pro Thr<br>120 125 130 | | 483 |
| GCC CAC CCC AGC CCC TCA CCC AGG TCA GCC GGC CAG TTC CAA ACC CTG<br>Ala His Pro Ser Pro Ser Pro Arg Ser Ala Gly Gln Phe Gln Thr Leu<br>135 140 145 | | 531 |
| GTG GTT GGT GTC GTG GGC GGC CTG CTG GGC AGC CTG GTG CTG CTA GTC<br>Val Val Gly Val Val Gly Gly Leu Leu Gly Ser Leu Val Leu Leu Val<br>150 155 160 165 | | 579 |
| TGG GTC CTG GCC GTC ATC TGC TCC CGG GCC GCA CGA GGG ACA ATA GGA<br>Trp Val Leu Ala Val Ile Cys Ser Arg Ala Ala Arg Gly Thr Ile Gly<br>170 175 180 | | 627 |
| GCC AGG CGC ACC GGC CAG CCC CTG AAG GAG GAC CCC TCA GCC GTG CCT<br>Ala Arg Arg Thr Gly Gln Pro Leu Lys Glu Asp Pro Ser Ala Val Pro<br>185 190 195 | | 675 |
| GTG TTC TCT GTG GAC TAT GGG GAG CTG GAT TTC CAG TGG CGA GAG AAG<br>Val Phe Ser Val Asp Tyr Gly Glu Leu Asp Phe Gln Trp Arg Glu Lys<br>200 205 210 | | 723 |
| ACC CCG GAG CCC CCC GTG CCC TGT GTC CCT GAG CAG ACG GAG TAT GCC<br>Thr Pro Glu Pro Pro Val Pro Cys Val Pro Glu Gln Thr Glu Tyr Ala<br>215 220 225 | | 771 |
| ACC ATT GTC TTT CCT AGC GGA ATG GGC ACC TCA TCC CCC GCC CGC AGG<br>Thr Ile Val Phe Pro Ser Gly Met Gly Thr Ser Ser Pro Ala Arg Arg<br>230 235 240 245 | | 819 |
| GGC TCA GCT GAC GGC CCT CGG AGT GCC CAG CCA CTG AGG CCT GAG GAT<br>Gly Ser Ala Asp Gly Pro Arg Ser Ala Gln Pro Leu Arg Pro Glu Asp<br>250 255 260 | | 867 |
| GGA CAC TGC TCT TGG CCC CTC TGACCGGCTT CCTTGGCCAC CAGTGTTCTG<br>Gly His Cys Ser Trp Pro Leu<br>265 | | 918 |
| CAG | | 921 |

What is claimed:

1. An isolated DNA molecule encoding a polypeptide having the amino acid sequence shown in SEQ ID NO:1.

2. The isolated DNA molecule according to claim 1, wherein said DNA molecule has the nucleotide sequence shown in SEQ ID NO:2.

3. The isolated DNA molecule according to claim 1, wherein said DNA molecule has the nucleotide sequence in SEQ ID NO:3.

4. A cloning vector comprising the isolated DNA molecule according to any of claims 1 to 3 operatively linked to an expression control sequence.

* * * * *